US009189613B1

(12) United States Patent
Tuthill et al.

(10) Patent No.: US 9,189,613 B1
(45) Date of Patent: Nov. 17, 2015

(54) SYSTEMS AND METHODS FOR AUTHENTICATING A USER WITH A DEVICE

(71) Applicant: Fitweiser, Inc., Las Vegas, NV (US)

(72) Inventors: Steve Tuthill, Eastvale, CA (US); Rudy Campidonica, Las Vegas, NV (US)

(73) Assignee: FITWEISER, INC., Las Vegas, NV (US)

( * ) Notice: Subject to any disclaimer, the term of this patent is extended or adjusted under 35 U.S.C. 154(b) by 0 days.

(21) Appl. No.: 14/337,139

(22) Filed: Jul. 21, 2014

Related U.S. Application Data

(63) Continuation-in-part of application No. 14/329,886, filed on Jul. 11, 2014, and a continuation-in-part of application No. 14/329,891, filed on Jul. 11, 2014.

(51) Int. Cl.
*G07F 17/32* (2006.01)
*A63F 13/10* (2006.01)
*G06F 21/32* (2013.01)
*G06Q 20/40* (2012.01)

(52) U.S. Cl.
CPC ............... *G06F 21/32* (2013.01); *G06Q 20/40* (2013.01)

(58) Field of Classification Search
USPC ........................................ 463/29, 30; 700/91
See application file for complete search history.

(56) References Cited

U.S. PATENT DOCUMENTS

| 2001/0023360 | A1* | 9/2001 | Nelson et al. .................... 607/60 |
| 2001/0031998 | A1* | 10/2001 | Nelson et al. .................... 607/60 |
| 2004/0092367 | A1 | 5/2004 | Corbalis et al. |
| 2007/0219059 | A1 | 9/2007 | Schwartz et al. |
| 2007/0225118 | A1 | 9/2007 | Giorno |
| 2009/0098981 | A1 | 4/2009 | Del Giorno |
| 2013/0127636 | A1* | 5/2013 | Aryanpur et al. ......... 340/870.07 |
| 2014/0005811 | A1* | 1/2014 | Mikan et al. .................... 700/91 |
| 2014/0149235 | A1* | 5/2014 | Gilley et al. .................... 705/15 |
| 2014/0247151 | A1 | 9/2014 | Proud et al. |

* cited by examiner

*Primary Examiner* — Pierre E Elisca
(74) *Attorney, Agent, or Firm* — Procopio, Cory, Hargreaves & Savitch LLP; Noel C. Gillespie

(57) ABSTRACT

Embodiments described herein provide for systems and methods for providing a user with an interactive, feedback-driven exercise program through the use of exercise equipment which provides tactile, visual and auditory feedback through proactive and reactive control, as well as portable electronic devices in communication with the exercise equipment to sense user activity, store user data and feedback for providing automated exercise program modifications, and provide visual and auditory feedback in the form of an interactive visual exercise experience using displays and other device feedback, as well as authenticate the user and user exercise equipment. The systems and methods are configured to create prescriptive exercises based on user profiles, which are then displayed to the user on the portable electronic devices during the execution of the exercise program on the exercise equipment.

16 Claims, 11 Drawing Sheets

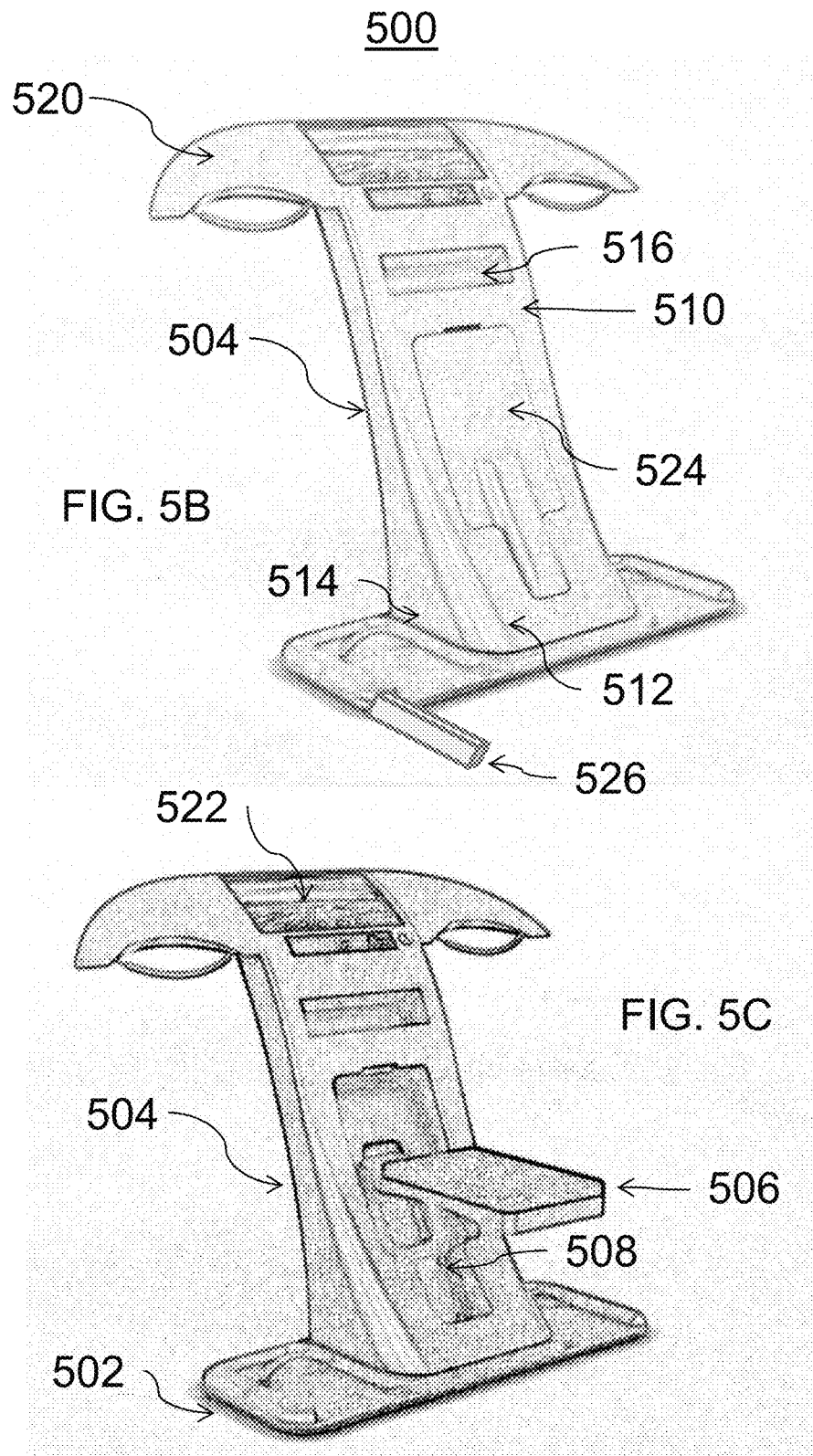

SYSTEMS AND METHODS FOR AUTHENTICATING A USER WITH A DEVICE

BACKGROUND

1. Field of the Invention

The systems and methods described herein relate generally to authenticating users and devices, and more specifically to authenticating devices and users for carrying out feedback-driven exercises using customized user profiles and devices.

2. Related Art

Existing exercise equipment is limited to simply displaying basic statistics relating to the performance of the user, such as distance traveled, force exerted or calories burned. Exercise devices are designed to perform the same way for every user, allowing minimal customization and providing little if any feedback to the user in relation to the exercise being performed.

As a result, many users also experience gym fatigue from the monotony of exercising in one place with an exercise machine that provides little or no interaction, feedback or entertainment. Although some exercise devices provide connections to audio or video provided by a nearby television or radio station, the content is unrelated to the exercise and has no effect on the user's performance.

Furthermore, while users adopt wearable sensors and electronics to monitor their own health and fitness, exercise devices have failed to integrate or adapt to these new technologies. Users are unable to integrate the information from their exercise devices with the information on their wearable devices, and often cannot integrate the information from their various wearable devices to understand the complete picture of their fitness.

Therefore, what are needed are systems and devices that overcome these significant problems found in the conventional systems as described above.

SUMMARY

Embodiments described herein provide for systems and methods for authenticating users and devices for providing an interactive, feedback-driven exercise program through the use of exercise equipment which provides tactile, visual and auditory feedback through proactive and reactive control, as well as portable electronic devices in communication with the exercise equipment to sense user activity, store user data and feedback for providing automated exercise program modifications, and provide visual and auditory feedback in the form of an interactive visual exercise experience using displays and other device feedback. The systems and methods are configured to create prescriptive exercises based on user profiles, which are then displayed to the user on the portable electronic devices during the execution of the exercise program on the exercise equipment. Exercise equipment is configured to interface with portable electronic devices to first authenticate the equipment and the portable electronic device before executing the prescriptive exercises and providing feedback to the user. Device authentication ensures the reliability and performance of the equipment and the devices. A user authentication process also requires the user to authenticate with the system via an identifying means through the portable electronic device or communication via the portable electronic device to a remote cloud server. Prior to initiating the exercise program, the user logs in through an application interface or other passive communication means and communicates with the cloud and authenticates the user's identity, connected devices and equipment, as well as user selected updates uploads and downloads. During the exercise program, feedback is provided from the portable electronic devices, exercise equipment and other sensors on or around the user, which are then fed back to one or more of the portable electronic devices for real-time feedback to the user. The feedback is also utilized by the exercise program or a program running on a remote server to update the exercise program based on the user's performance, and to update the user's profile.

In one embodiment, a method of providing an interactive, feedback-driven exercise program comprises: creating at least one user profile; developing at least one exercise program based on the user profile; transmitting the at least one exercise program to a portable electronic device connected with an exercise device for executing the at least one exercise program; receiving performance feedback with regard to the user's performance of the at least one exercise program; and generating response feedback in response to the received performance feedback.

In another embodiment, a method of dynamically modifying an exercise program based on user feedback comprises: receiving performance feedback with regard to a user's performance of at least one exercise program; modifying the at least one exercise program based on the user's performance; transmitting the modified at least one exercise program to a portable electronic device connected with an exercise device; and executing the modified at least one exercise program on the exercise device.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which:

FIGS. 5B and 5C are illustrations of third configuration of the exercise device, according to an embodiment of the invention;

DETAILED DESCRIPTION

Certain embodiments disclosed herein provide for systems and methods for providing a user with an interactive, feedback-driven exercise through the use of exercise equipment which provides tactile, visual or auditory feedback through proactive and reactive control, as well as portable electronic devices in communication with the exercise equipment to sense user activity, store user data and feedback for providing automated exercise program modifications, and provide visual and auditory feedback in the form of an interactive visual exercise experience using displays and other device feedback. The systems and methods are configured to create prescriptive exercises based on user profiles, which are then displayed to the user on the portable electronic devices during the execution of the exercise program on the exercise equipment. During the exercise program, feedback is provided from the portable electronic devices, exercise equipment and other sensors on or around the user, which are then fed back to one or more of the portable electronic devices for real-time feedback to the user. The feedback is also utilized by the exercise program or a program running on a remote server to update the exercise program based on the user's performance, and to update the user's profile.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

I. Interactive Exercise System

Figure 1:
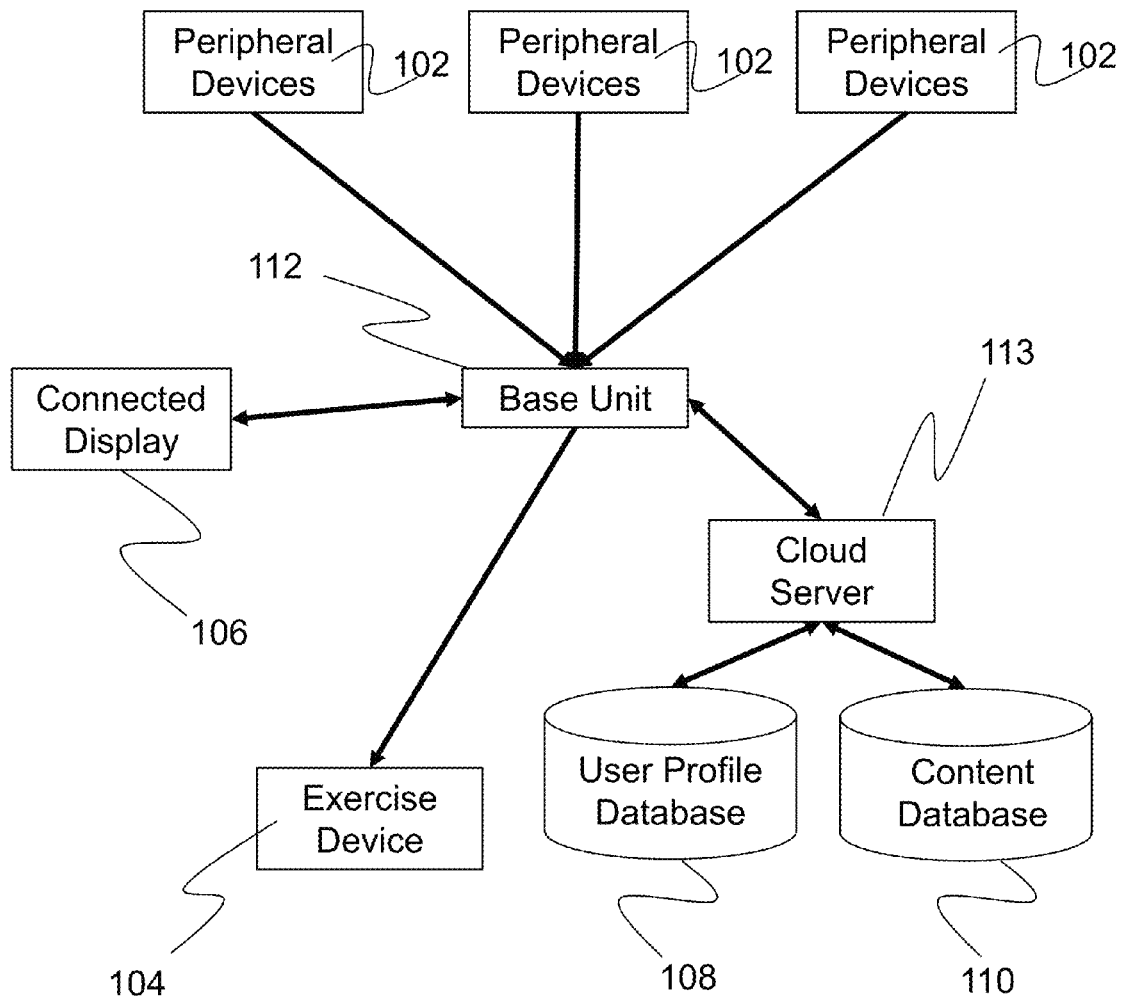
FIG. 1 is a block diagram illustrating an interactive exercise system including an exercise device and a plurality of connected devices and displays for providing an interactive, feedback-driven exercise program, according to an embodiment of the invention.

One embodiment of an interactive feedback-driven exercise system is illustrated in FIG. 1, and includes an exercise device 104 configured to provide feedback to a user; a plurality of peripheral devices 102 in communication with the exercise device 104 to communicate instructions to the user for an exercise program and provide feedback to the exercise device regarding user performance. The exercise device 104 is provided with a motor controller configured within the exercise device to translate the exercise program and user feedback relating to the exercise program into feedback to the user. A base unit 112 may be connected with the exercise device 104 and may be a fixed or portable computing device which controls and manages all of the interactions between the exercise device 104, peripheral devices 102, connected displays 106 and databases 110, as will be described below.

A connected display 106 may be provided to display a graphical user interface to the user during the performance of the exercise program, including information on the user's performance or entertainment information that provides visual interactions with the user to keep the user engaged with the exercise program. For example, the connected display may be a virtual reality display device, which provides a virtual reality environment to the user related to the performance of the exercise program.

The exercise device may also be connected with one or more databases which store information, such as a content database 110 which stores information and can stream exercise program content or a user profile database 108 which stores information on a user profile that is used to configure the exercise programs specifically for each user. The databases may be integrated within the base unit itself, or, as in FIG. 1, accessible via a cloud server 113 at a remote location from the base unit 112.

The peripheral devices 102 may include one or more wearable devices which sense user activity, including motion, physiological data such as heart rate, blood pressure, etc. and report the information back to the base unit 112 which in turn, communicates with the exercise device 104 for altering the exercise program based on this feedback.

Figure 2:
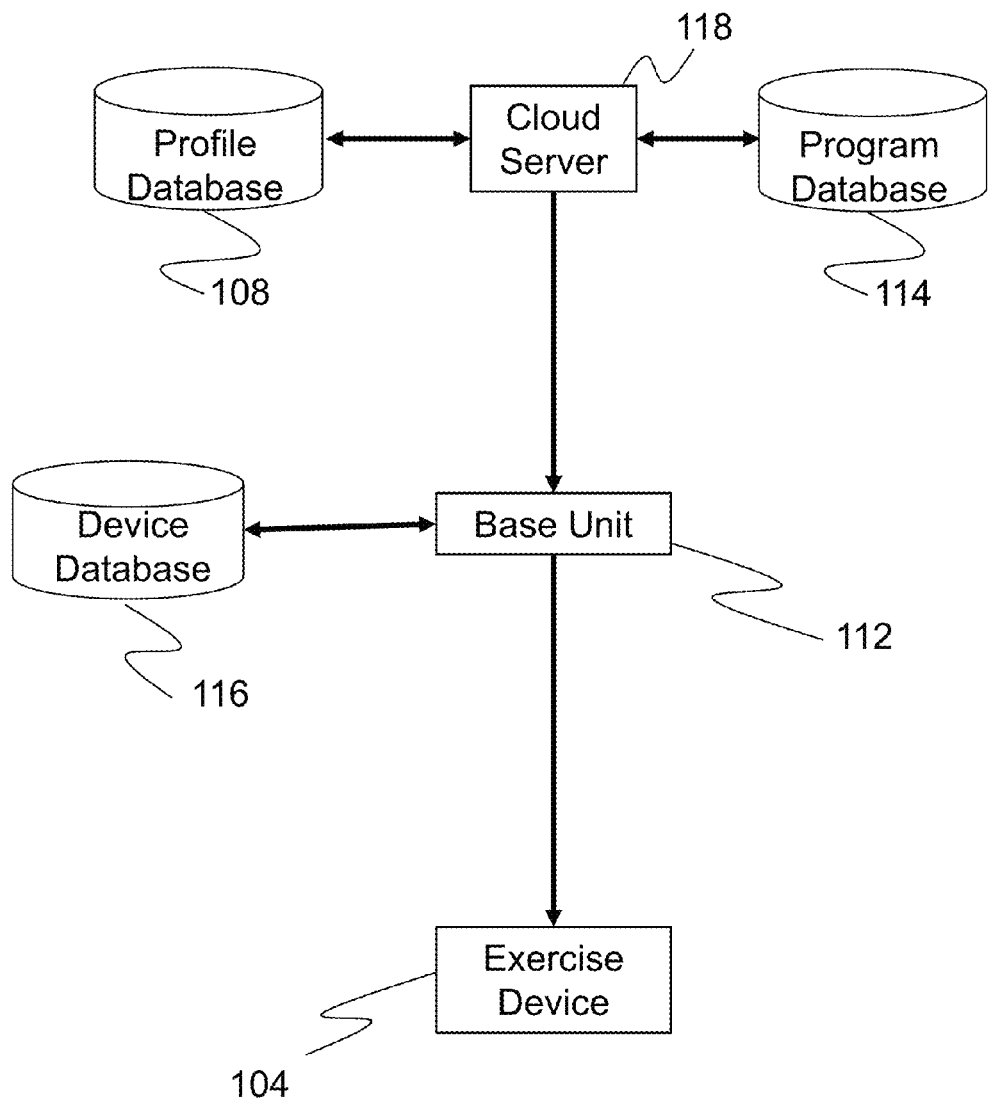
FIG. 2 is a block diagram illustrating a further example exercise system, according to an embodiment of the invention.

An alternate exercise system is illustrated in FIG. 2, where the exercise device is connected with a cloud server 118 that allows the exercise device to access a program database 114 of the exercise programs or the profile database 108 of users and their customized programs. A device database 116 may be connected with the exercise device 104 directly to provide a list of the devices that may be worn by or connected with the users and provide feedback information so that the exercise device 104 can connect with and receive information from these devices during the execution of the exercise program.

II. Peripheral Sensors and Display Devices

In one embodiment, the peripheral devices 102 may be wearable devices and sensors, such as smart watches, bracelets or even sensors embedded into clothing, shoes, etc. The peripheral devices 102 will be configured to communicate with the exercise device 104 and any connected displays 106 to display the user activity during the exercise program. The exercise device 104 may then adjust the feedback provided to the user based on the information obtained from the peripheral sensors to either increase or decrease resistance, difficulty, etc.

The connected display 106 may include display devices such as a smartphone, tablet, computing device, television or monitor, virtual reality display such as goggles or eyeglasses, etc. that provide visual information to the user. The connected display may be incorporated into the exercise device or remotely mounted at a separate location in the area, or, as with a virtual goggles device, worn by the user.

III. Feedback Exercise Device

An interactive reconfigurable exercise device 300 is illustrated in FIGS. 3-5C, and comprises a reconfigurable feedback-driven interaction portion which provides feedback to a user during a performance of at least one exercise program, such as physical, tactile or haptic feedback; a visual feedback portion which provides visual feedback—such as audio or video feedback—to the user relating to the performance of the at least one exercise program; and a controller which communicates with the reconfigurable interaction portion and visual feedback portion to control an amount of the feedback provided by the interaction portion.

Throughout this embodiment, the exercise device may also be referred to as a hardware platform, which in this embodiment is a mechanical-for-force transmission system that transmits resistance from one or more motors to upper and lower cables independently.

In one embodiment, the hardware platform 300 is embodied by a base 302, a tower 304 and a reconfigurable portion 306, which in this embodiment is a seat. The hardware platform 300 may employ a motor-controller 308 within the tower 304 or base 302 and one or more cable/pulley/spool motors 310 to provide resistance to a cable/pulley/spool 312 utilized by a user for exercise. Additionally, a tower indicator section 314 on the tower 304 and a corresponding software indicator control provide interactive resistance control through the motor controller 308. Separate take-up spools may be used to independently actuate each cable or pulley. A dashboard section 316 may be configured to dock, mount or retain the base unit 112. Wired or wireless connectors such as Bluetooth, NFC, USB or other connection types will provide communication with the base unit smart devices and the hardware platform 300. The Base Unit Smart devices may be smartphones and tablets, and may operate on a mobile operating system such as iOS or Android. Signals between the base unit and hardware platform 300 will be bidirectional.

The on-board motor controller 308 interacts with the hardware and software applications and serves as an interface controller that applies resistance commands to various resistance motors, transmissions, clutches, electromagnets, etc. to apply resistance to cables, discs, and the like, and provides forced feedback based on user/app interaction. The hardware platform 300 with the motor controller 308 may provide movement of an add-on module in an X, Y, or Z axis. As will be described in further detail below, the reconfigurable portion 306 is mounted to the base 302 on a universal mount 318, which is capable of being fitted with a plurality of different exercise modules to provide for the performance of different exercises.

The hardware platform, with various add-on modules, is intended to assist in building strength, joint and muscle flexibility, range of motion of individual limbs, sense of balance and stability. It may also perform rehabilitation functions, sports and movement training, balance and other physical therapies.

Figure 4:
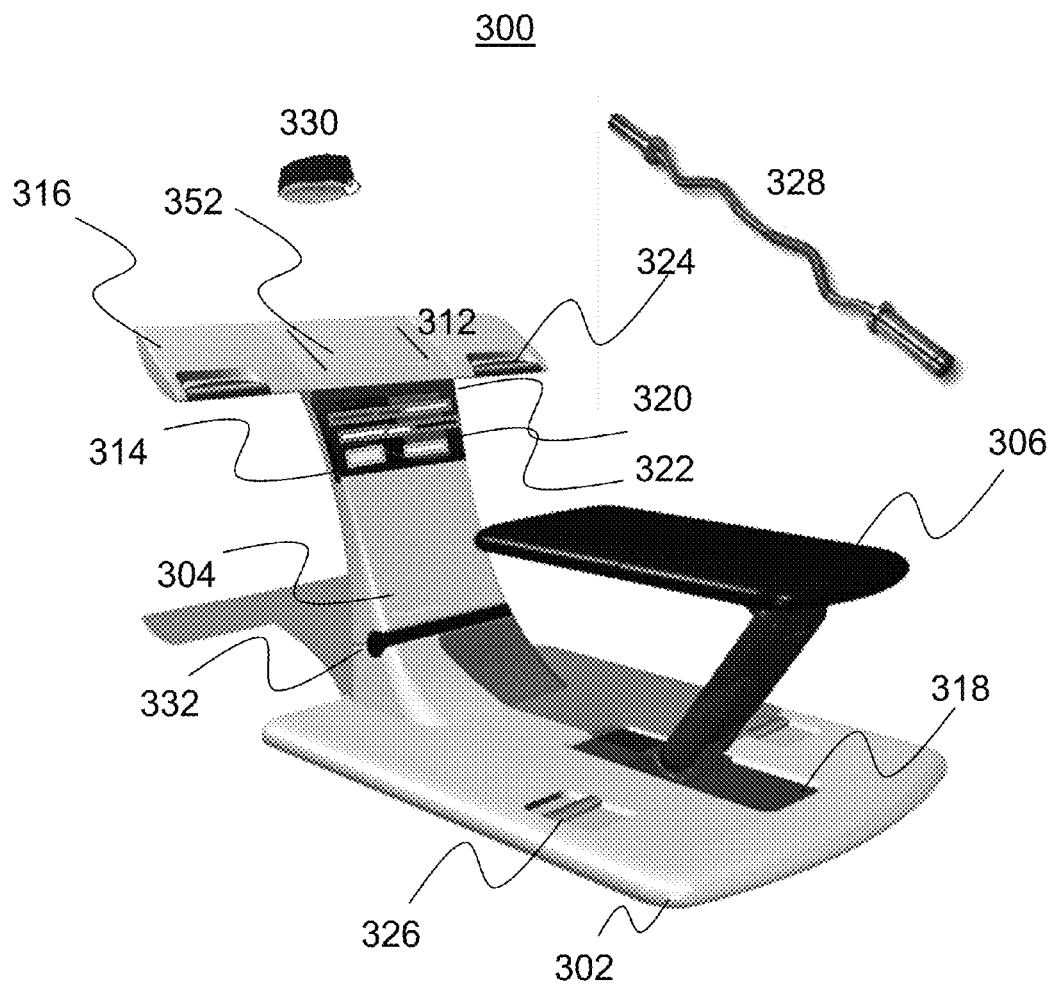
FIG. 4 is a perspective-view illustration of a first configuration of the exercise device, according to an embodiment of the invention.

Specific components of the hardware platform are listed below and illustrated in FIG. 4, including indicator lights 320 and a visual display 322 on the tower indicator section 314. As shown in FIG. 4, the cables 312, located in the dashboard and tower, are gripped with cable handles 324, and the cables 312 may be mounted at different positions on the hardware platform, such as the lower cable handles 326 on the base 302. In one embodiment, direct current powers the electrical drive modules and the controller, although AC power may be used as well. A power supply is mounted within the tower, and standard household current connection plugs in from the tower.

All lights turn off when the machine is powered off. A built-in safety feature is that the hardware platform shuts off after five minutes of non-operation.

The onboard motor controller 308, located within the tower 304 as a sensor link, is responsible for actuating and measuring cable resistance and position of the cables within the dashboard 312 and tower 304, as well as controlling other resistance devices, such as electromagnets, enabling bidirectional communication with the hardware platform apps through attached/paired base unit smart devices.

Forced Feedback: An onboard motor controller program provides resistance in concert with apps. Forced feedback may be a tactile feedback technology, which takes advantage of the sense of touch by applying forces, vibrations, or motions to the user through the cables and auxiliary add-on devices, such as, bikes, platforms, sports gear, etc. In one embodiment, the hardware platform enables, at a minimum, weight settings with control over the right side and left side individually and in combination.

Bluetooth/USB: Wired or wireless connections to smart devices enable communication through the onboard motor controller 308 or other electronics, i.e., motherboard. The USB connection enables smart devices to be charged and can serve as communication link.

Pairing: In one embodiment, establishing a connection between smart device/app and the hardware platform enables users to easily establish communication between the smart device and the on board motor controller (through Bluetooth or USB connector).

Calibration: Calibration operations may be performed to assure that the apps and motor controller functions are connected and are operational in a synchronous real time environment. Real time response between apps and the resistance devices on the hardware platform is imperative for acceptable user experience.

Universal Mount: The universal mount 318 on or within the base 302 attaches and secures a "removable" seat 306 and other future modules. The universal mount will also accommodate a wire harness with electric power and communications with the motor controller for future modules. The modules may include other types of exercise devices, including an exercise bar 328 or leg strap 330, but also including bicycles, skis, oars, or even a baseball bat, golf club, tennis racquet, etc.

Tower Smart Device Dock 352: Located in the center space between the cable handles on the dashboard 316, the dock 352 provides a secure, no-slip holder for smart phones and tablets. In addition, it may house a connector such as a USB connector.

Handle Drop Safety Consideration: In one embodiment, if a user drops any cable handle while under tension, the resistance stops momentarily and then slowly retracts the handles to their stored position.

A folding hinge 332, in this configuration, enables the folding and unfolding of the tower 304. The hinge 332 should lock securely to counter the pull exerted by the cables. Any wiring routed to the tower that is exposed when folded is to be protected from accidental pinching or other actions detrimental to Hardware platform safety and operation.

Figure 5A:
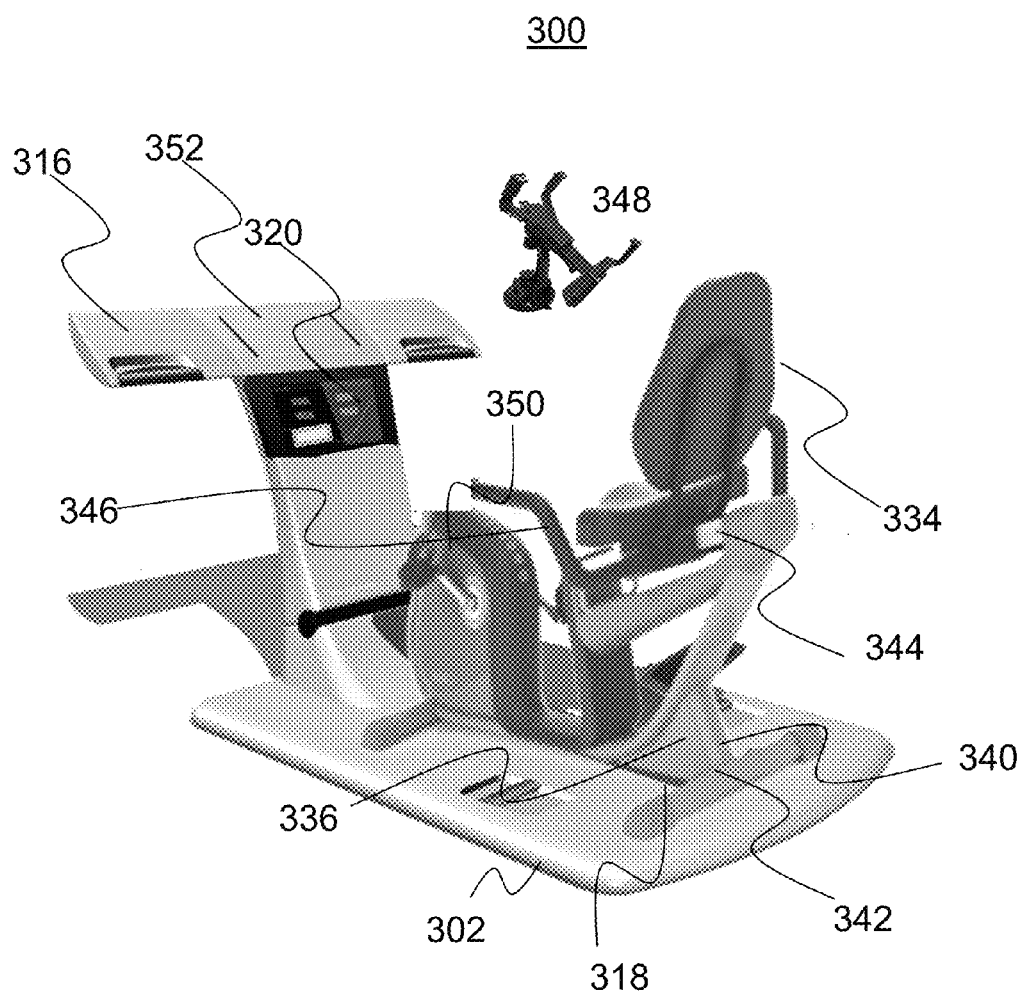
FIG. 5A is a perspective view illustration of a second configuration of the exercise device, according to an embodiment of the invention.

FIG. 5A illustrates an alternative configuration of the hardware platform 300 with a bicycle module 334 connected via the universal mount 318. The bicycle module 334 includes a frame assembly 336 to unite the base 302 with the bicycle module 334 and a receiver 338 for the universal mount 318. A rear stabilizer attachment 340 and a rear stabilizer bar 342 may also be incorporated into the bicycle module 334 to provide stability during operation. The bicycle module 334 may also be configured with a seat adjustment pin 344 to adjust the seat, and hand grips 346 with heart rate contacts to monitor a user's heart rate during an exercise. FIG. 5 also illustrates one embodiment of a smart device base unit mount 348 that is configured to mount to a flywheel pedal assembly 350 on the bicycle module.

Figure 3:
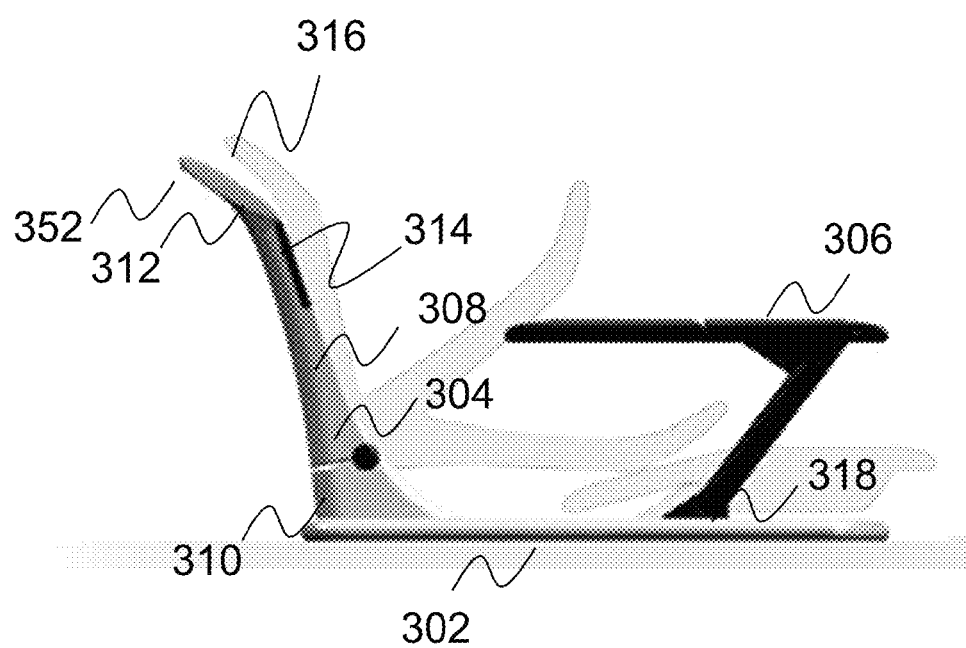
FIG. 3 is an side-view illustration of an example exercise device, according to an embodiment of the invention.

In another embodiment illustrated in FIG. 5B and FIG. 5C, the hardware platform 500 is embodied by a smaller base 502 than the base 300, FIGS. 3-5, a tower 504 a reconfigurable portion 506, which in this embodiment is a seat with its universal mount 508. The hardware platform 500, may employ a motor-controller 510 within the tower 504 and one or more cable/pulley/spool motors 512 to provide resistance to a cable pulley spool 514 utilized by a user for exercise. In this embodiment the seat 506 is able to fold into the tower as shown in 524. A stabilizer bar 526 is shown partially extended on the left side of the base 502 and retracted on the right side of the base 502. Additionally, a tower indicator section 516 on the tower 504 and a corresponding software control provide interactive resistance control through the motor controller

510. Separate take-up spools may be used to independently actuate each cable or pulley. A dashboard selection 520 may be configured to doc, mount or retain the base unit FIG. 2, 112 in the center portion of the dashboard 522. Wired or wireless connectors such as Bluetooth, NFC, USB or other connection types will provide communication with the base unit smart devise and the hardware platform. The Base Unit Smart devices may be smartphones and tablets, and may operate on a mobile operating system such as iOS or Android. Signals between the base unit and hardware platform 500 will be bidirectional.

IV. General Description and Operation

In one embodiment, exercise is achieved by pulling one or two cable handles 324 under a resistance load. In one embodiment, the cable handles 324 are located at four positions, two upper cable handles 324 located in the dashboard 316 and two lower cable handles 326 on the base platform 302 (floor). In one embodiment, each side may provide up to 200 pounds on each motor, providing a total of up to 400 pounds of weight resistance.

One embodiment of the hardware platform machine is composed of the following features described below:

The Hardware platform 300 consists of an upright body (tower 304 and dashboard 316) with resistance sources, the removable seat assembly 306 and the base platform 302. The base platform 302 is supported on two front casters; and it is sufficiently narrow for transporting the machine through 30" wide doors.

The seat 306 can be unfolded to form a bench for exercises in various orientations. The seat is locked in place at various heights to accommodate short and tall users. The removable seat assembly includes a reclined backrest for support and bracing during specific exercises. The seat and tower can be folded, in this configuration, for storage.

A dock 352, in the center of dashboard 316, is provided for placing a base unit (FIG. 1, 112), such as a smart phone or tablet, will be located in the dashboard 316. Communication with the base unit smart device 112 will be via Bluetooth or a USB connector also located in the tower 304. The USB connector(s) will also attach to the devices placed in the dock.

The exercise bar 328 fits into either the upper cable handles or lower cable handles; and it can be securely attached to either the upper cable handles 324 or lower cable handles 326. The leg strap accessory 330 is attached to the user's ankles for leg exercises.

V. Motor Control

Users connect their paired and calibrated base unit smart device 112 to the tower and select an interactive program on an application running on the base unit 112 designed to work with the hardware platform 300. The program may be stored in the program database 114 at the remote cloud server 113 and accessed over a network. Indicator lights 320 provide status of power, Internet connectivity, and hardware platform operational readiness. Selected apps on the smart devices provide visual displays and produce/react to bidirectional signals relayed to the app through the hardware platform onboard motor controller that provides multiple types of feedback to the user by responsive hardware platform cables 312. In another embodiment, other resistive devices may be employed to provide alternative types of feedback, such as electromechanical controlled or servo-controlled add-on modules. The result is the change in resistance consistent with the smart device displays in real-time.

Electrical Cable Drive

In one embodiment, the electrical drive and the motor control interface for generating the resistance force are positioned in the base of the tower structure 304. Each of the two upper cables attached to the upper cable handles 324 may reel out from the tower 304 approximately five to six feet. The two lower cables attached to the lower cable handles 326 may reel out approximately six to nine feet. Cable reels, pulleys, spools, a gear or transmission or clutch, or electromagnet, and the servomotor with sensors are tied together, perhaps on a common or separate axis, and they compose the electrical drive module. All of these components are known as the electrical cable drive system.

In operation, variable current, and thereby torque, is applied to the servomotor. These affect the cable resistance force, while unreeling and reversing the cable.

The motor controller executes commands for cable resistance, and measures distance and velocity communication as provided by the instructions from the smart device apps, and responds with feedback (forced, haptic, visual, audio, etc.) to application outputs to affect resistance and direct difference exercise regimes. One or more sensors within the motor controller sense the extended length of cable per millimeter. The sensors are also integral to measure speed and distance of cable movement i.e., how rapidly and how far the cable moves in both directions, as well as the angle of the cable. These bidirectional signals will be responsive to user interaction with apps with real-time interactivity and may be coupled with a motion tracking device to help determine, along with the motor controller information, whether the exercise is being performed correctly In one embodiment, the electrical cable drive will have latency under 100 ms when interacting with visual media.

The user is able to select different exercise regimes using an application running on the smart device, which then controls the motor controller. The motor controller also provides feedback to the smart device and the application on the device as to the performance of the user with the equipment. The performance of the cable drive will eliminate (a) any backlash or dead stretches during reel-out and (b) cogging sensation, while applying smooth force to the handles.

VI. Cable Forces

In one embodiment, the maximum bi-directional forces on the cable at the handle attachment location are up to 200 lbs. per side when pulled simultaneously or up to 400 lbs. when pulled separately from the bottom handles and for the upper handles.

When pulled simultaneously, both the upper and lower cables will provide a maximum bi-directional force of up to 200 lbs. per handle for a total of up to 400 lbs. When any one of the four cables is pulled by itself, it will provide a maximum bi-directional force of up to 200 lbs. Various contributors of friction, including from the drive assembly itself, shall be included in these values. In one embodiment, the net lowest force setting may be 2 lbs. In one embodiment, friction force at the cable termination shall not exceed 2% of used force during cable extension and 2.5% of force during retraction. The maximum force in both directions may be equal, or the retraction force may be set to a lesser or greater value, as set by the application controlling the motor controller located in the tower structure. The forces in both directions may change linearly or within a prescribed curve. The force levels may reset themselves for a specific exercise. The force level may then be maintained, once motion has slowed and arrived at standstill.

The force level may change and direction of force shall change with slack-off of motion to zero prior to reverse cable motion. The resistance level can be set to zero until the handles are positioned for any specific exercise to be programmed into the motor controller. The force on any handle will drop to zero if a handle is released suddenly by the user.

In one embodiment, a force curve may be used to execute a prescriptive exercise where a resistive force on the cable increases as the user pulls the cable and then decreases half way through the pulling motion. For example, the initial resistive force at the beginning of the pull may be 0 lbs of force, increase gradually to 40 lbs of resistive force in the middle of the pull, and then decline back to 0 lbs of resistive force by the end of the pull.

VII. Dimensions and Range of Motion

In one embodiment, the dimensions of the exercise device may be provided as follows: Platform width max.: 27.5 inches; Platform base length: 60-72 inches (The platform base may need to have the length increased in order to accommodate future modules.); Overall length (use): 73-85 inches; Overall length (for stowing): 64-76 inches; Overall height (stowed): 15 inches; Platform thickness: 2 inches; Height from platform top to upper cable exit: 30 inches; Usable cable extension length: 108 inches for lower cable and 72 inches for upper cable. Range of Motion, in one or more embodiments shall mean utilization of prescribing or measuring and tracking angles, bidirectional resistance forces, and velocity of cables or future module extension and retractions, tracking, bidirectional resistance forces, and velocities.

Drive Motors

In one embodiment, the electrical drive motor or motors 310 shall be mounted within the tower structure, although the motors may be located in any part of the hardware platform 300 depending on the configuration of the platform or the type of workout device attached with the platform.

The drive motor assembly, when installed, shall permit heat dissipation within the tower through conduction, convection, louvered ventilation, or other means. Tower surfaces shall not generate heat beyond 95 degrees F., under the environmental conditions. The drive motor and cabling shall be electromagnetically shielded, when installed.

All cable wiring harnesses shall terminate in reliable connectors at the mating interfaces of modules. Such cabling includes power, control and auxiliary equipment routing including smart devices, as well as communication with all external apps, via Bluetooth or USB.

The drive motor assembly is to fit within the tower confines, which are planned to be 4×12 inches or less. The modular approach permits easy access and exchange of the drive motor or drive motor components/modules without affecting the installed force cable assembly. For design considerations, the motor control board(s), any potential motherboard, or other circuitry could be mounted behind the LED indicator light panel for easy maintenance.

Mobility

Since the end user will operate the hardware platform machine in bedrooms and other living environments, it is suited for simple fold-up and move for stowage, also transporting through nominally 30-inch wide door openings (effectively 28 inches).

The machine, as assembled for transport, shall move on two rollers, which are mounted under the platform proper at the tower end. Each roller shall have a capacity of 150 lbs. and be non-marking on floors or carpets. The casters shall be effectively contacting the ground for rolling, when the platform is tilted upward 30-45 degrees.

Stiffness and Backlash

The user wants smooth extension and retraction of the cable. Excessive dither and jitter, backlash and structural flexure are objectionable, however subjective.

With the user standing anywhere on platform and applying 400 lbs. force on one or two cable handles, the tower and platform flexure shall not be perceptible by the user, i.e. not to exceed ½ inch total.

Note that for structural and component design, the stiffness criteria (rather than strength) may determine design and sizing. Modular interfaces may need to incorporate shear locators and shear connectors to provide rigid mounting under load, rather than relying only on bolted or welded assembly methods.

All fasteners will have self-locking features continuing to function after five assembly operations. All electrical harness and other connectors shall function reliably after five connections and disconnections.

VIII. Interaction Portion—Platform and Mount

As illustrated in FIGS. 3-5, the hardware platform 300 is designed for easy attachment to the Universal Mount 318 on or within the Hardware Platform. The attachment process includes attaching the Wire Harness from the hardware platform and securing modules, such as the bicycle module 334 with a Key Pin or other securing method, such as slots, pins, or retractable pins, which fit into the slots. Seat adjustments will be an easy to use incline ramp to increase and decrease the distance from the pedals.

Performance

The hardware platform machine is planned as a base platform and allows for upgraded add-on features over time. These considerations are included in the Onboard Motor Controller Functional Specs below.

Onboard Motor Controller Functional Specs

The function and features of the hardware platform onboard motor controller 308 shall be as follows:

1. Bi-directionally control and accurately measure cable resistance, force, direction, velocity, and position/angle levels from the four points of handles on the upper tower and lower portions of the base handles.

2. Communicate with smart devices using Bluetooth and USB

3. Easily pair and calibrate with smart device phones and tablets

4. Communicate and respond to app outputs for forced feedback with latency under 100 ms 5. Measure cable extension and retraction by millimeters with accurate fidelity 6. Maximize measurement per second with latency under 100 ms 7. Maximize resistance, force, direction, velocity, and position from app output The Onboard Motor Controller 308, as a sensor link, is responsible for actuating and measuring cable resistance and position, as well as controlling other resistance devices, such as electro magnets, enabling bidirectional communication with Hardware platform apps through attached/paired smart devices.

Smart Device Communication

The Motor Controller 308 must communicate with the base unit FIG. 1, 112, including smartphones and tablets, using any proprietary or known operating systems, including iOS and Android operating systems. Future operating systems may include Windows and others.

Seat/Bench Positions

The removable seat/bench assembly shall be finely height adjustable and safely lockable from 16 to 20.5 inches above the platform in minimum increments of 0.5 inches and firmly attached to the universal mount with mounting pins. The seat shall support a maximum weight of 300 lbs. The seat shall not move perceptively from an upward or sideways exercise force of 200 lbs. Seat should rotate 360 degrees with locks at 180-degree positions to facilitate using the seat back as a part of exercise back support when required.

The forward portion of the bench shall be settable in an upward rotated position to enable a person to stand while exercising in between bench and tower. The seat should be designed to be easily removable.

The bench/seat top surface shall be cushioned and not feel unpleasant to touch when exposed to perspiration.

A universal seat mount 318 will be designed on the hardware platform 300 to accept future modules, as well as the base model seat. The universal seat connector will include both a mechanical connector and a wire harness with the following input/output: 110V power, 48V DC power. All cable wiring harnesses shall terminate in reliable connectors at the mating interfaces of modules. Such cabling includes power, control and auxiliary equipment routing including smart devices and apps and Bluetooth and USB. In one embodiment, the universal seat mount 318 could have a plurality of contact points which each represent a different type of device. For example, if five total contact points are available, a certain type of seat mount may use three of the connections in a specific pattern to identify which device is being connected, while another type of mount may use three connections in a different pattern, or four connections instead of three.

User Exercise Assist and Accessories

In one embodiment, cable attached accessories include: handles attached to cable that are easily replaceable and sold as a replacement accessory; one exercise bar, approx. 40" long; and two foot straps for leg exercises.

The machine shall be powered by nominally single phase 110+/−10 Volt, 60+/−5 Hz and selectable 220+/−10 Volt 50+/−5 Hz. A grounding connection shall be included.

Two separate power cord connectors shall service the two types of power. This facilitates adaptation of plug-in connection to various countries' particular connection requirements, by simply supplying an appropriate power cord.

Other foreign power compatibility requirements may be added.

The machine shall tolerate and survive without damage brownout conditions and momentary spikes and variations in voltage and frequency from nearby lightning and other such effects.

Drives, Controls/Computer and Auxiliary Devices

Considerations for drives, controls/computer and auxiliary devices will focus in two distinct areas. The first area is the collective drives, controls/computer and auxiliary devices in the hardware platform that enable motor controller and user app outputs from and inputs to users' smart devices to direct or record, as directed, the different exercise regimes with variable: resistance, force, direction, velocity, and position/angle along with forced feedback. Bi-directional signals will be responsive to user interaction with apps with real-time interactivity.

A sensor will detect the extended length of cable in each of the four cables measured in millimeters. In addition, the sensor is used for speed sensing, i.e., how rapidly the cable moves in both directions. This input will be communicated to the smart device via Bluetooth and USB connections.

The second area is connections that are in a ready state for auxiliary modules. Power to the auxiliary module, communication for bi-directional control signals to and from smart devices and the auxiliary module, and real time enabled response for resistance settings is inherent in both the stand alone hardware platform and in conjunction with the modules. In addition, the signal for bi-directional communication will enable signals from the hardware modules concurrent with the hardware platform to enable, as an example, resistance and forced feedback to the pedals attached to the exercise bike module, as well as to the hand held cables in the hardware platform.

If needed for limiting spikes, a separate transformer may supply the motor controller as powering motor, smart devices, and add-on modules.

Sufficient current shall be available for all electrical and electronic equipment, without making changes for the hardware base platform model, including any auxiliary devices and add on modules.

IX. Assessments, Profiling and Feedback

Figure 7A:
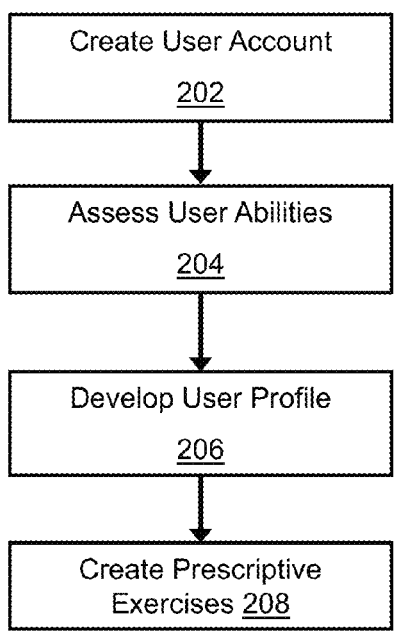
FIG. 7A is a flow diagram illustrating a method of developing an prescriptive exercise program based on a user profile, according to an embodiment of the invention.

In one embodiment, a method of using the system of FIG. 1 and FIG. 2 (below) to develop interactive, feedback-driven exercises are illustrated in FIG. 7A. As shown in FIG. 7A, the methods include the ability for the user to create an account for storing their profile and payment information (step 202), equipment registration and authentication, user(s) registration with name, password, physiological verification strategies including fingerprint(s), biological vitals, smart chip/dongle, and third party verification for financial transactions (steps 203 A-203 E), assessing the user's health or fitness (step 204) to then develop and update a user profile (step 206). With the user profile, the system can create specifically-configured exercise programs (step 208), known herein as pre-scriptive exercises, that are based on the user's health, fitness and stored exercise information, and which are updated based on the feedback generated during the performance of the exercise programs, as will be described immediately below.

Figure 7B:
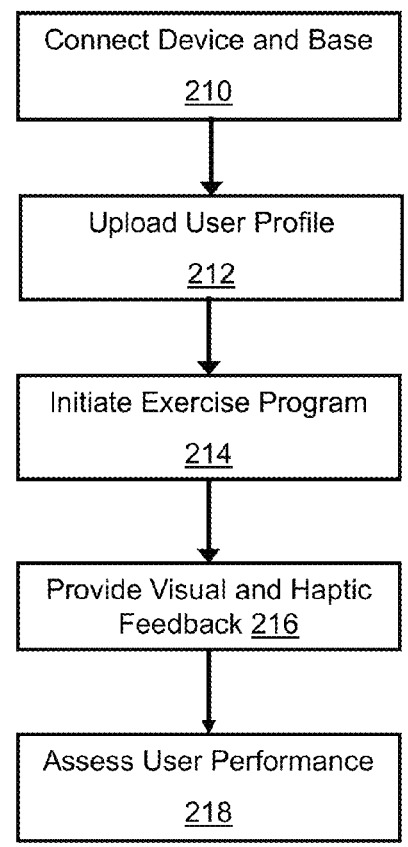
FIG. 7B is a flow diagram illustrating a method of providing feedback to a user during an exercise program, according to an embodiment of the invention.

During the execution of an exercise program, as illustrated in FIG. 7B, the user is provided with visual and haptic feedback from the exercise device, connected displays and peripheral devices, which all operate to provide the user with an interactive experience that monitors the user and keeps the user engaged and interested in the exercise program. The user begins by connecting the base unit smart device to the exercise device (step 210), which then accesses the user's profile (step 212) (either from a local database on the base unit or via the remote server and user profile database) and communicates with the exercise device to initiate an exercise program for the user to perform (step 214). The base unit, exercise device and any other connected displays or peripheral devices will then provide instructions to the user in the form of tactile, visual or auditory feedback (step 216) that will guide the user through the exercise program. This may also include presenting the user with a virtual environment that simulates a real-world exercise or location for the exercise that will better engage and motivate the user to complete the exercise program. Feedback may also be provided to the exercise program or the remote cloud server by the exercise device, base unit and any other wearable or surrounding sensors on or about the user as to the user's performance of the exercise program. These sensors may track the user's movements, strength, biometrics or other physiological conditions to determine whether the user is completing the exercise program as intended and whether the user is improving overall health or fitness. In one embodiment, the sensors may be embedded in the exercise equipment, such as a sensor in a bat, golf club, tennis racquet, etc. which tracks the user's swing and overall movement. This feedback is then utilized by an application on the base unit smart device or the cloud server to assess the user's performance (step 218).

Figure 7C:
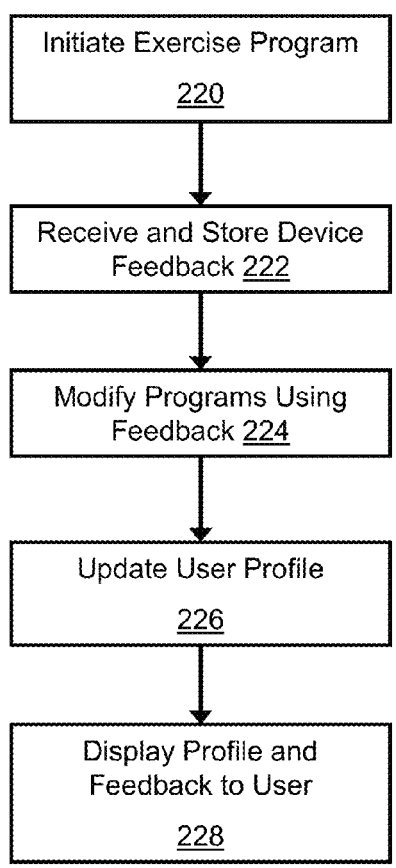
FIG. 7C is a flow diagram illustrating an example process for modifying exercise programs based on feedback, according to an embodiment of the invention.

FIG. 7C illustrates a method of modifying the exercise program and user profile based on the feedback. In step 220, the exercise program is initiated and the user begins to perform the prescriptive exercises. Feedback from the exercise equipment and one or more sensors is then received at the base unit or remote cloud server, where it is stored (step 222). Next, an application running on the base unit or remote cloud server will modify the exercise program based on the feedback (step 224), such as increasing the requirements if the user is improving, or decreasing the requirements if the user is not improving. The user profile and corresponding exercise programs is then updated (step 226), after which the updated profile and exercise programs can be displayed to the user on the base unit or another visual display (step 228). The user may be presented with performance statistics, comparisons with other users, overall records for certain exercise programs, and recommendations for other exercise programs based on performance. The user display may also be in the form of auditory or visual alerts, such as push notifications to the base unit smart device or a graphical overlay of the user's performance in comparison with the average of other users.

In one embodiment, the feedback is used to modify the exercise program in real time to provide an instant adjustment if the user is struggling to complete the program or if the user is too easily completing the program without much effort.

X. Prescriptive Exercises

The system is configured to utilize the exercise device and connected peripherals to develop prescriptive exercises for each individual user. The prescriptive exercises may be based on the performance of the user during past exercises, an assessment or evaluation of the user's health or fitness, or the user's profile information that the user submits or has completed by a health or fitness professional.

The prescriptive exercises may incorporate different combinations of the exercise device with connected displays and peripheral devices to accomplish specific tasks, and of course incorporate the haptic feedback of the exercise device to provide a realistic exercise experience. In one embodiment, the prescriptive exercises may not be tied to a particular piece of exercise equipment, and may be programs which simply require the user to perform specific movements or use unconventional objects to perform the exercise program (such as a chair, table, desk, bed, etc.). The portability of the prescriptive exercises is important for users that may want to perform their exercise program in any location and may not have access to a traditional exercise device. In one aspect, the user may be able to input the available objects and have the system respond with exercise programs that utilize those objects.

The prescriptive exercises may be stored as exercise programs either on the user's smart device or in the program database or content database on the cloud server of the systems illustrated in FIG. 1 and FIG. 2.

XI. Multi-User Concurrent Exercise Programs

In one embodiment, the exercise programs may be configured to be performed by multiple users at the same time, so that users in the same or different locations can compete against each other in competitive-style exercise programs. For example, the exercise equipment may utilize the bicycle module in FIG. 5 and have the users race against each other during the exercise program while using one or more visual displays to display graphics of a race track and a virtual avatar of the other racers. The data of the other users may be streamed across the user interfaces on the one or more visual displays. In one embodiment, the hardware platform may be configured with a customized universal mount that is capable of mounting an actual bicycle and connecting the bicycle to sensors so that the users can exercise in place on their own bicycles.

XII. Virtual Trainer

In one embodiment, the user may be provided with a virtual trainer through the connected displays and base unit that provides motivation and instruction to the user during the exercise programs. The virtual trainer may be customized to a user's personality, gender, types of exercises, etc. in order to provide the user with a motivating, immersive exercise experience.

XIII. User Interfaces and Feedback

Figure 6:
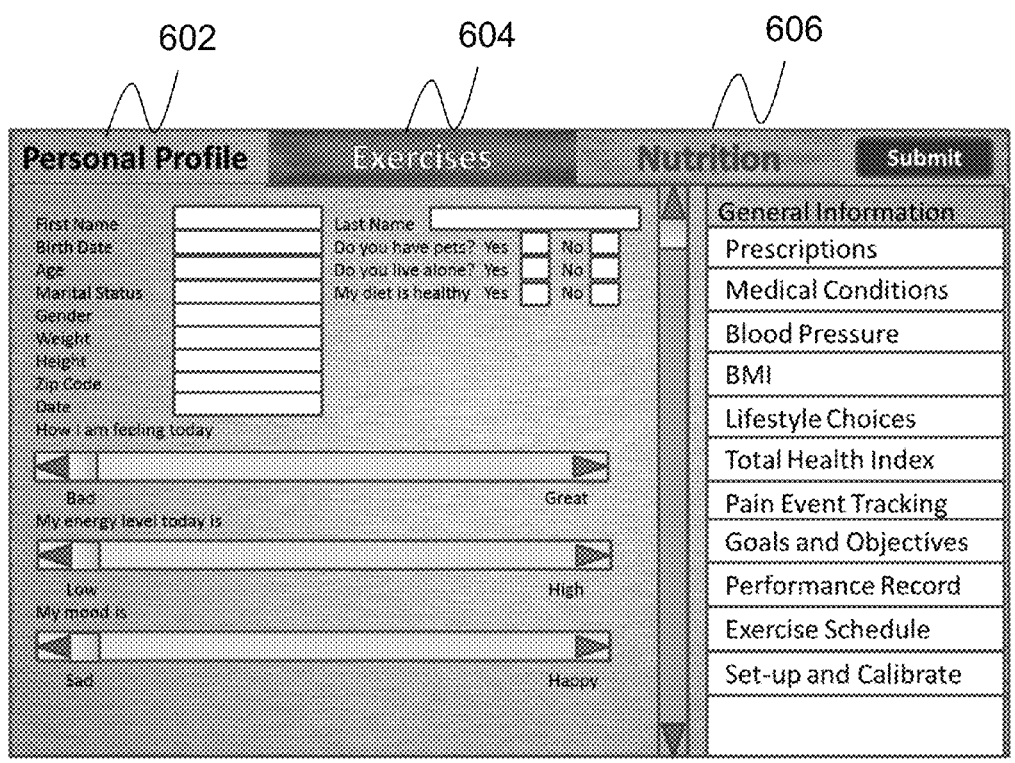
FIG. 6 is a graphical user interface of a user profile for storing exercise data and managing exercise programs, according to an embodiment of the invention.

One embodiment of a graphical user interface 600 is illustrated in FIG. 6, where the user is provided with information on their user profile and exercise programs, including information on their health and physiological information in a personal profile tab 602, exercise program information and details in an exercise tab 604, and nutrition information in a nutrition tab 606. These GUIs may be presented to a user on the base unit or a connected display or device and will be continually updated during the performance of exercise programs or updates from the user on their health and fitness.

XIV. Authentication and Payments

Figure 7D:
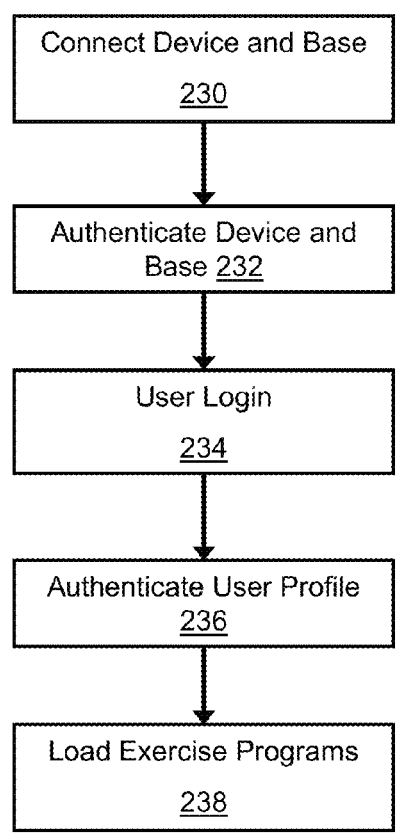
FIG. 7D is a flow diagram illustrating an example process of authenticating a user, exercise equipment and portable electronic device.

In one embodiment illustrated in FIG. 7D, a method provides the ability to connect the exercise device and base device (such as a smartphone or other user device) and other peripherals (step 230) to authenticate both the device and base with each other (step 232), and allow the user to login in step 234 and authenticate their user profile with the cloud server (step 236) before loading their customized exercise programs (step 238). The authentication feature will ensure that only the paying user is able to access their profile and customized exercises.

A method of connecting the exercise equipment and base device to authenticate the devices and user is illustrated in FIG. 7D, where after the user creates the user account (step 202), the user proceeds to the step of registering the exercise equipment with the base device and authenticating the user with the system (step 203). Within the registration process, separate steps are provided whereby authentication protocols are established (step 203A), the serial numbers of the exercise equipment are identified and transmitted to the system for authentication (step 203B), and the user is authenticated by entering their user name, password or other verification information (such as biometric or physiological) (step 203C). These authentication steps may also be carried out using a chip, card or dongle strategy (step 203D), or a separate third party authentication (step 203E).

Figure 7E:
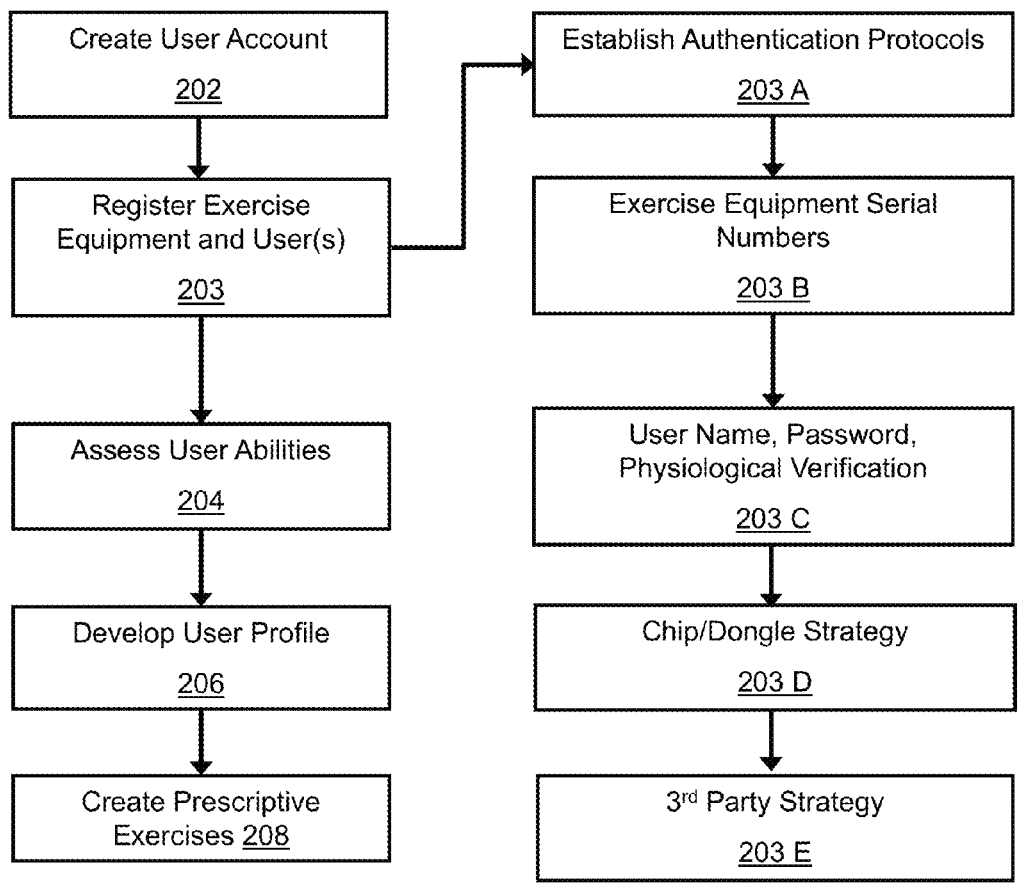
FIG. 7E is a flow diagram illustrating a process of registering and authenticating a user with the exercise equipment.

FIG. 7E illustrates the steps carried out during the registration of the equipment, devices and users in step 203 of FIG. 7A, above. Authentication protocols are established (step 203A) to determine the type of authentication that will be required. Next, the exercise equipment is authenticated by providing a unique serial number of the equipment to the device or cloud server to verify that it is an authentic piece of equipment (step 203B). Once the equipment is authenticated, a user is authenticated by requesting the user name, password or other identifying feature (such as a unique card, chip, device, or physiological or biometric feature) of the user (step 203C). In one embodiment, the user may authenticate with the system using a chip or dongle (step 203D) carried on the person or embedded within the user's clothing, worn on the skin, etc. In another embodiment, a third party may handle the authentication strategy (step 203E) to guarantee security of the authenticating information.

Additional authentication features may be provided for payment and purchasing of new programs, equipment, wearable devices and displays and even services related to the devices. This authentication will allow a service provider such as a gym or clinic to have a remote server authenticate the user and provide payment services without requiring their own system or protocol for payment and authentication, since it will be completed through the illustrated system in FIGS. 1 and 2 described below. As described briefly above, one embodiment of the system provides software for authenticating the user with the exercise device for access and payment. The authentication allows the user to access any exercise device at any location and upload their user profile information, exercise programs and physiological and nutrition information, which will then be tailored for the exercise programs the user is executing.

XV. Computer-Enabled Embodiment

Figure 8:
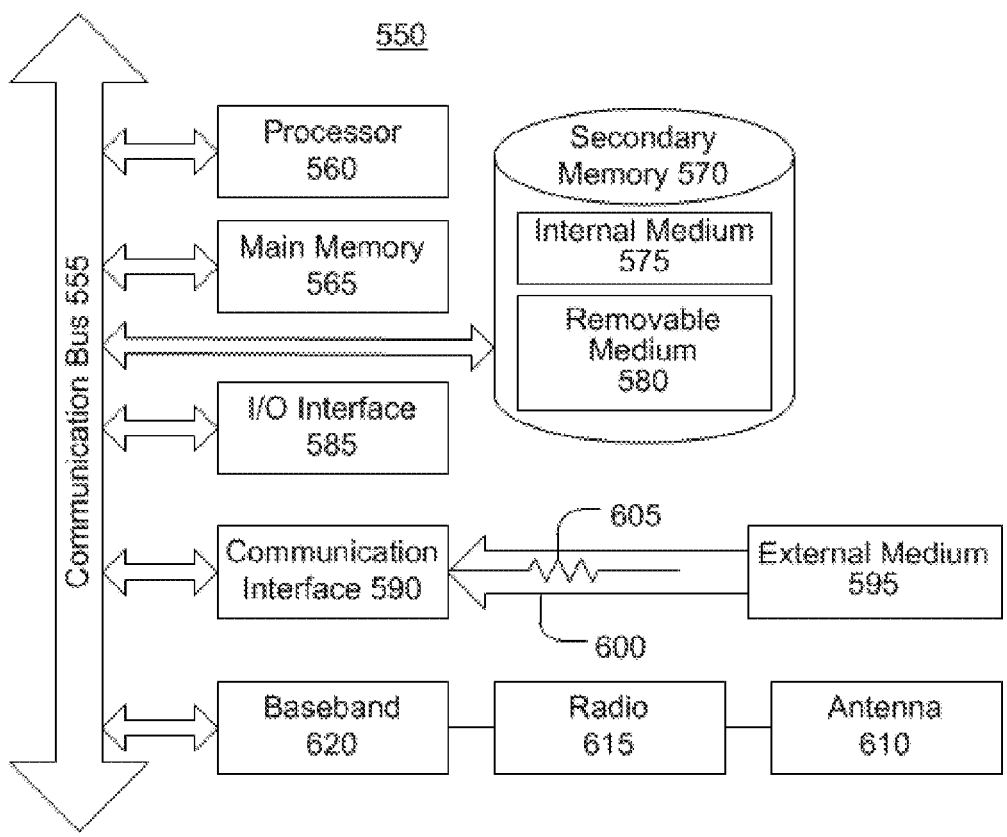
FIG. 8 is a block diagram illustrating an example wired or wireless processor enabled device that may be used in connection with various embodiments described herein.

FIG. 8 is a block diagram illustrating an example wired or wireless system 550 that may be used in connection with various embodiments described herein. For example the system 550 may be used as or in conjunction with an interactive haptic feedback exercise device as previously described with respect to FIGS. 1-6B. The system 550 can be a conventional personal computer, computer server, personal digital assistant, smart phone, tablet computer, or any other processor enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

System 550 preferably includes a main memory 565 and may also include a secondary memory 570. The main memory 565 provides storage of instructions and data for programs executing on the processor 560. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include a internal memory 575 and/or a removable medium 580, for example a flash memory (USB) drive, reprogrammable and removable firmware, EEPROM, a compact disc ("CD") drive, a digital versatile disc ("DVD") drive, etc. The removable medium 580 is read from and/or written to in a well-known manner. Removable storage medium 580 may be, for example, a flash memory (USB) drive, reprogrammable and removable firmware, EEPROM, CD, DVD, SD card, etc.

The removable storage medium 580 is a non-transitory computer readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 570. Examples of external storage medium 595 may include an external hard disk drive or an external optical drive, or and external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media 580 and communication interface 590, which allow software and data to be transferred from an external medium 595 to the system 550.

System 550 may also include an input/output ("I/O") interface 585. The I/O interface 585 facilitates input from and output to external devices. For example the I/O interface 585 may receive input from a keyboard or mouse and may provide output to a display. The I/O interface 585 is capable of facilitating input from and output to various alternative types of human interface and machine interface devices alike.

System 550 may also include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a modem, a network interface card ("NIC"), a wireless data card, a communications port, a PCMCIA slot and card, an infrared interface, and an IEEE 1394 fire-wire, just to name a few.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570 in any smart device, firmware or other device. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

The system 550 also includes optional wireless communication components that facilitate wireless communication over a voice and over a data network. The wireless communication components comprise an antenna system 610, a radio system 615 and a baseband system 620. In the system 550, radio frequency ("RF") signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown) that are executable by processor 560.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

The invention claimed is:

1. A method of authenticating users and exercise devices through remote or proximal servers and the use of synchronous data exchange between stored exercise programs or environments where dynamic images are sent to a user display and resistance and other exercise equipment settings are modified through a motor controller in response to user active and reactive responses with a plurality of inputs to the stored exercise programs or environments enabling for an interactive, visual and physical feedback-driven exercise system, the method comprising:
   connecting at least one piece of exercise equipment through at least one portable electronic device;
   authenticating the at least one piece of exercise equipment through the at least one portable electronic device using a unique identifier or other means on the at least one piece of exercise equipment;
   authenticating a user through the at least one portable electronic device by communicating with a remote server or servers containing authentication information of the user;
   loading at least one exercise program or exercise environment from the remote server to or through the at least one portable electronic device with instructions to a motor controller that performs exercise system settings for execution on the at least one piece of exercise equipment once the authentication is complete;
   and displaying authorization verification and at least one exercise program or environment to a user.

2. The method of claim 1, wherein the user authenticates through the at least one portable electronic device using a wirelessly communicating dongle or sensor that has embedded user identification verified with a remote server.

3. The method of claim 2, wherein the sensor is a wearable device that that provides synchronous information and indicates a user's physical state, including heart rate or galvanic skin response or other user physical state for transmission to a remote server or to an exercise system as input to at least one exercise program or visual environment program, where the information is processed, and transmitted through a communication device to an exercise system and provides outputs such as modification of equipment settings and/or user display.

4. The method of claim 3, wherein the wearable device is embedded within an item of clothing.

5. The method of claim 1 wherein a communication dongle or sensor is an item of jewelry that assists in the user authorization process with user identification transmitted to a remote server used in conjunction with other user identification means.

6. The method of claim 1, wherein the authentication of the user enables a user to make a purchase with the at least one portable electronic device.

7. The method of claim 1, wherein the user authenticates using a physiological property.

8. The method of claim 1, wherein the user authenticates using a biometric parameter.

9. The method of claim 1, wherein the at least one piece of exercise equipment is authenticated using a serial number.

10. The method of claim 1, wherein the authentication of the device is provided by a remote server.

11. The method of claim 1, wherein the user and users exercise equipment are authenticated by user smart device communication to remote server user data storage.

12. A method in claim 1 where visual feedback is a dynamic environment that reacts synchronously with a user to display environmental images in conjunction with communicated equipment settings to a motor controller for modification including resistance and/or x, y, z coordinate change based on user active and reactive inputs to the dynamic environmental images.

13. A method in claim 12 where visual feedback is through virtual reality display.

14. A method in claim 1 where user feedback is immersive including visual, haptic and tactile feedback as well as kinesthetic and mechanical stimulation with attributes including multi-sensory, proximal environmental, bodily, and force multimodal interaction.

15. A system for authenticating user purchases through a remote server(s) comprising:
   at least one user;
   at least one portable electronic device in communication with the at least one remote server;
   a second remote server in communication with the at least one portable electronic device;
   wherein the at least one user interactively communicates identifying information to remote server(s) via the at least one portable electronic device to authenticate the at least one user or a purchase;
   and wherein the system for authenticating users comprises three levels where the first level includes at least a user name and password or user identification within a device or dongle, a second level with at least a biometric component, and a third level that includes a second remote server that executes transmission of stored user supplied data dates, locations, alphanumeric strings, and other data that is randomly selected and presented to a user requiring user interpretative responses that when validated result in authorization transmissions to involved parties in the forms of display or transmitted data.

16. The system of claim 15, wherein the at least one portable electronic device communicates with a remote server to authenticate a user of an exercise system prior to executing an exercise program or environment on the at least one piece of exercise equipment and user display.

* * * * *